United States Patent
Edavana et al.

(10) Patent No.: US 9,615,985 B2
(45) Date of Patent: Apr. 11, 2017

(54) DIRECT DRIVE TILT MECHANISM FOR INFANT-CARE MEDICAL DEVICES

(71) Applicant: KONINKLIJKE PHILIPS N.V., Eindhoven (NL)

(72) Inventors: Roopesh Edavana, Bangalore (IN); Melwyn Dominic Dmello, Bangalore (IN)

(73) Assignee: Koninklijke Philips N.V., Eindhoven (NL)

( * ) Notice: Subject to any disclaimer, the term of this patent is extended or adjusted under 35 U.S.C. 154(b) by 231 days.

(21) Appl. No.: 14/416,459

(22) PCT Filed: Jul. 12, 2013

(86) PCT No.: PCT/IB2013/055747
§ 371 (c)(1),
(2) Date: Jan. 22, 2015

(87) PCT Pub. No.: WO2014/024062
PCT Pub. Date: Feb. 13, 2014

(65) Prior Publication Data
US 2015/0202104 A1    Jul. 23, 2015

(30) Foreign Application Priority Data
Aug. 8, 2012  (IN) ............... 3252/CHE/2012

(51) Int. Cl.
  *A61G 11/00* (2006.01)
  *A61F 7/00* (2006.01)
(52) U.S. Cl.
  CPC .............. *A61G 11/008* (2013.01); *A61F 7/00* (2013.01)
(58) Field of Classification Search
  CPC .... A61G 11/00; A61G 11/001; A61G 11/005; A61G 11/008
  USPC ...................................... 600/21–22
  See application file for complete search history.

(56) References Cited

U.S. PATENT DOCUMENTS 5,244,452 A   9/1993  Vaccaro et al.
6,880,188 B1  4/2005  Schmidt et al.

FOREIGN PATENT DOCUMENTS

| CN | 2452482 Y   | 10/2001 |
| EP | 711537 A1   | 5/1996  |
| EP | 743054 A2   | 11/1996 |
| EP | 0968698 A2  | 1/2000  |
| JP | 2001070365 A | 3/2001 |
| WO | 0224138 A2  | 3/2002  |

*Primary Examiner* — John Lacyk (57) ABSTRACT

A system and method for tilting an infant-supporting device can be decoupled through a manual coupler or decoupler, that includes a clevis (40) coupled to the lifting means (4, 9) and a pivot pin (41) slidably coupled to the tilt means (12).

15 Claims, 5 Drawing Sheets

DIRECT DRIVE TILT MECHANISM FOR INFANT-CARE MEDICAL DEVICES

CROSS-REFERENCE TO PRIOR APPLICATIONS

This application is the U.S. National Phase application under 35 U.S.C. §371 of International Application No. PCT/IB20123/055747, filed on Jul. 12, 2013, which claims the benefit of Indian Patent Application No. 3252/CHE/ 2012, filed on Aug. 8, 2012. These applications are hereby incorporated by reference herein.

The present disclosure pertains to systems and methods for tilting infant-care medical devices, and, in particular, for maintaining the integrity of the environments around infants during adjustments to the tilt angle of infant-supporting devices.

It is well known that infants are vulnerable to infections, and bacterial organisms, viral organisms, and other pathogenic organisms that can cause infections. At least in some cases, these can be transmitted through airborne transmission of ambient air containing contaminated particles. It is known to use an incubator, baby warmer, infant-supporting device, and/or infant-care medical device for infants, e.g. neonates, in intensive care environments or elsewhere, e.g. to maintain an environment with an appropriate temperature, air flow, humidity, sterile conditions, and/or other environmental conditions. Environments that commonly employ incubators and/or baby warmers, such as, e.g., hospitals, commonly are plagued by a wide range of pathogenic organisms. It is known that some infants may, under certain conditions, benefit from being positioned at a tilted angle rather than on a flat surface. For example, head end elevation may prevent gastro esophageal reflux (GER) in preterm infants. Foot end elevation may benefit neonates having cardiac failure.

Accordingly, it is an object of one or more embodiments of the present invention to provide a system for tilting an infant-supporting device having a thermo-regulated area. The system comprises a tilt platform, a housing, a support member, an actuator, and a manual coupler. The tilt platform is configured to be disposed below the infant-supporting device. The tilt platform is configured to tilt about a tilt axis. The housing is disposed below the tilt platform. The support member is held by the housing, the support member providing support to the tilt platform to maintain a rotational orientation of the tilt platform about the tilt axis. The support member is held by the housing such that a position of the support member with respect to the housing is adjustable. Adjustment of the position of the support member with respect to the housing adjusts the rotational orientation of the tilt platform about the tilt axis. The actuator is operable to adjust the position of the support member with respect to the housing, thereby adjusting the rotational orientation of the tilt platform. The actuator is disposed and actuated outside of the thermo-regulated area of the infant-supporting device. The manual coupler couples the tilt platform to the support member. Adjustment of the position of the support member is accomplished through the manual coupler. The manual coupler is configured to decouple the tilt platform from the support member by receiving manipulation.

It is yet another aspect of one or more embodiments of the present invention to provide a method for supporting an infant with an infant-supporting device using a system having a tilt platform disposed below the infant-supporting device, an actuator, a support member, a housing disposed below the tilt platform, and a manual coupler that couples the tilt platform to the support member. The method comprises holding the support member by the housing such that a position of the support member with respect to the housing is adjustable through actuation received by the actuator, wherein adjustment of the position of the support member with respect to the housing adjusts a rotational orientation of the tilt platform about the tilt axis, and wherein adjustment of the position of the support member is accomplished through the manual coupler; providing support to the tilt platform by the support member to maintain the rotational orientation of the tilt platform about the tilt axis; and decoupling the tilt platform from the support member by receiving manipulation through the manual coupler.

It is yet another aspect of one or more embodiments to provide a system configured to support an infant with an infant-supporting device. The system comprises tilt means, housing means, lifting means, support means, actuator means, and coupling means. The tilt means disposed below the infant-supporting device is for tilting the infant-supporting device about a tilt axis. The lifting means has a position with respect to a housing means that is disposed below the tilt means. The position of the lifting means is adjustable. Adjustment of the position with respect to the housing means adjusts a rotational orientation of the tilt means about the tilt axis. The support means provides support to the tilt means to maintain the rotational orientation of the tilt means about the tilt axis. The actuator means for receiving actuation. Actuation of the actuator means adjusts the position of the lifting means with respect to the housing means, thereby adjusting the rotational orientation of the tilt means. The coupling means is for coupling the tilt means to the support means. Adjustment of the position of the lifting means with respect to the housing means is accomplished through the coupling means. The coupling means is configured to decouple the tilt means from the support means by receiving manipulation.

It is yet another aspect of one or more embodiments of the present invention to provide a system for tilting an infant-supporting device. The system comprises a tilt platform, a housing, a non-rotating lead screw, and an actuator. The tilt platform is configured to be disposed below the infant-supporting device. The tilt platform is configured to tilt about a tilt axis. The housing is disposed below the tilt platform. The non-rotating lead screw is held by the housing, the non-rotating lead screw providing support to the tilt platform to maintain a rotational orientation of the tilt platform about the tilt axis. The non-rotating lead screw is held by the housing such that a position of the non-rotating lead screw with respect to the housing is adjustable. Adjustment of the position of the non-rotating lead screw with respect to the housing adjusts the rotational orientation of the tilt platform about the tilt axis. The actuator is operable to adjust the position of the non-rotating lead screw with respect to the housing, thereby adjusting the rotational orientation of the tilt platform.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
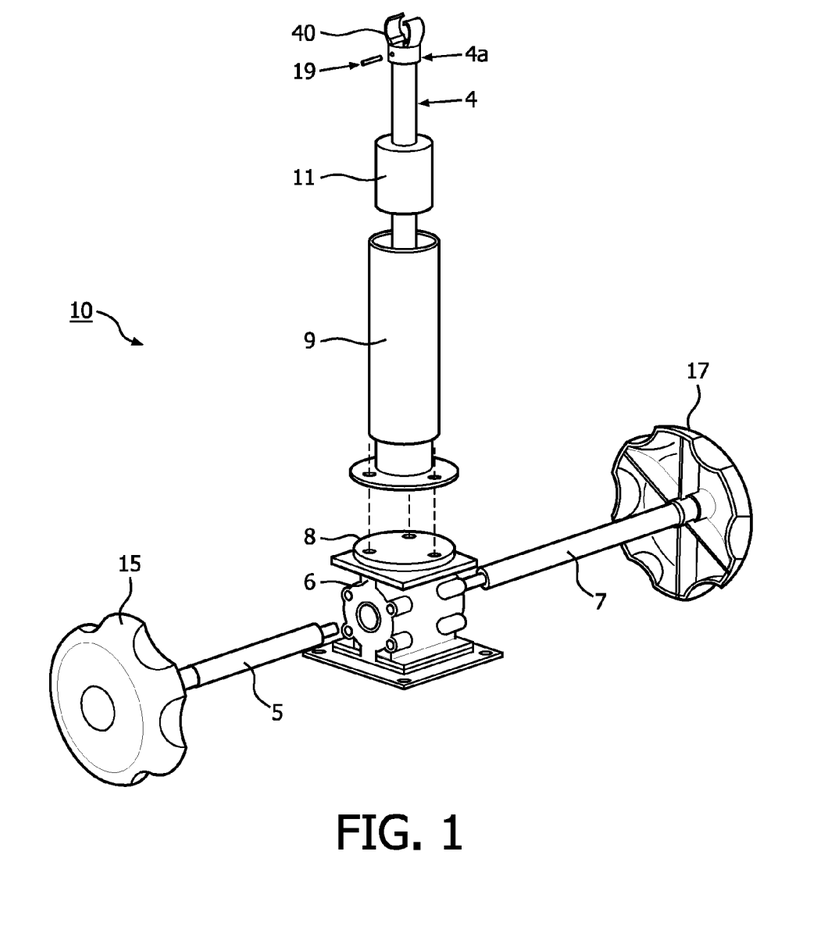
FIG. 1 illustrates various components of a system for tilting in accordance with one or more embodiments.

FIG. 1 illustrates an exploded view of various components of a tilt system 10 for tilting in accordance with one or more embodiments in a vertically exploded view. Tilt system 10 includes one or more of a first actuator 15, a second actuator 17, a housing 9, a support member 4, a first rod 5, a second rod 7, a gearbox 6, a mounting plate 8, a nut 11, a dowel pin 19, a clevis 40, and/or other components.

Figure 3:
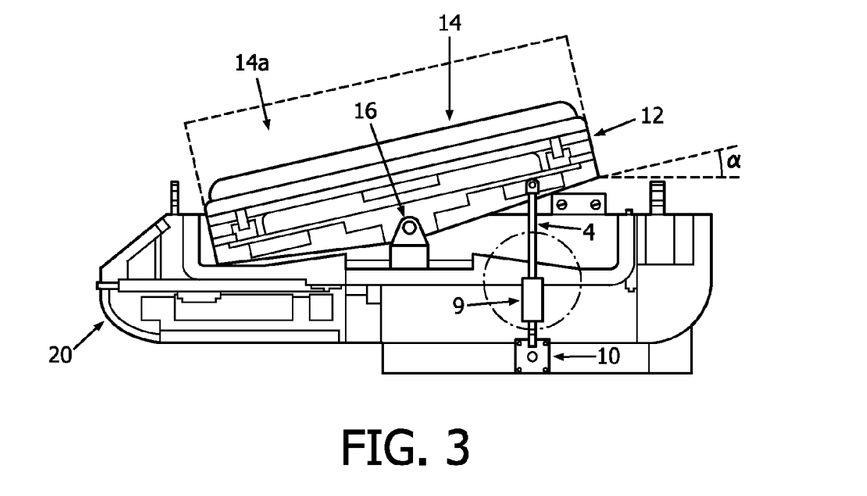
FIG. 3 illustrates a cross-section of an infant-supporting device in accordance with one or more embodiments.

As illustrated in FIG. 3, tilt system 10 may be integrated with an infant-care medical device 20, for example an incubator or baby warmer. Infant-care medical device 20 and/or tilt system 10 may include one or more of a tilt platform 12, an infant-supporting device 14, and/or other components. As used for the purposes of this disclosure, the term "infant" may refer to a neonate, an infant, a newborn, a baby, and/or other terms for a subject small enough to fit in an incubator or baby warmer. Tilt platform 12 is configured to tilt about a tilt axis 16 responsive to an adjustment of the position of support member 4. For example, the adjusted position may be the longitudinal position. Infant-supporting device 14 may include one or more of a bed, a mattress, a pad, a blanket, and/or other suitable structure to support an infant. Tilt platform 12 is disposed below infant-supporting device 14 such that tilting tilt platform 12 tilts infant-supporting device 14 correspondingly. Housing 9 is disposed below tilt platform 12. Infant-care medical device 20 and/or infant-supporting device 14 include an area 14a that may be a thermo-regulated area, sterile area, and/or an area within which a suitable environment is intended to be maintained for the benefit of an infant. This suitable environment may be referred to as a micro-environment for incubators and as a macro-environment for baby-warmers. Area 14a may encompass a three-dimensional area or volume. Environmental factors may include temperature, airflow, gas composition near an infant, humidity, light conditions, protection from pathogenic organisms, harmful particles and/or contamination. For example, in some embodiments, tilt system 10 may be integrated in an incubator such that the thermo-regulated area may comprise the area, volume, and/or enclosure enclosed by a hood of the incubator, and/or the area under tilt platform 12. Due to tilt system 10 being compact, operation of tilt system 10 may have a small or negligible effect on thermoregulation within area 14a, in contrast to existing tilt systems. Additionally, due to compactness and placement with respect to infant-care medical device 20, use of tilt system 10 as described herein allows under-surface phototherapy as may be used to treat hyperbilirubinemia. As used herein, "under-surface" may refer to a surface of infant-supporting device 14, e.g. a baby warmer.

Referring to FIG. 1, adjustment of the (longitudinal) position of support member 4 is initiated when first actuator 15 and/or second actuator 17 receive actuation. In some embodiments, first actuator 15 and/or second actuator 17 may be implemented as knobs capable of receiving actuation, e.g. in the form of rotational motion, from, e.g., a caregiver. Actuation of first actuator 15 and/or second actuator 17 may be transferred and/or converted to an adjustment of a position of support member 4 with respect to housing 9. Support member 4 is held, e.g. mechanically, by housing 9, e.g. such that support member 4 passes through housing 9. In some embodiments, support member 4 is a lead screw. Other (mechanical) couplings between housing 9 and support member 4 are contemplated. Support member 4 may include a distal end 4a that provides support to a tilt platform to maintain a rotational orientation about a tilt axis. Support member 4 may be held by housing 9 such that a longitudinal position of support member 4 with respect to housing 9 is adjustable longitudinally. Adjustment of the position of support member 4 adjusts the rotational orientation of a tilt platform about its tilt axis.

In some embodiments, first actuator 15 may be coupled through rod 5 to gearbox 6 such that actuation received by first actuator 15 is transferred and/or converted through rod 5 to motion within gearbox 6, and, subsequently, transferred and/or converted to motion of mounting plate 8 which is coupled to gearbox 6. Alternatively and/or simultaneously, second actuator 17 may be coupled through rod 7 to gearbox 6 such that actuation received by second actuator 17 is transferred and/or converted through rod 7 to motion within gearbox 6, and, subsequently, transferred and/or converted to motion of mounting plate 8 which is coupled to gearbox 6. Gearbox 6 may for example be a T type bevel gearbox. The couplings involving gearbox 6 may be mechanical couplings. In some embodiments, tilt system 10 may include two actuators that are coupled to the same rod. The motion of mounting plate 8 may be a rotational motion. Housing 9 may be coupled to gearbox 6 through mounting plate 8 such that rotational motion of mounting plate 8 may be transferred and/or converted to rotational motion of housing 9. Nut 11 may be affixed within and/or integrated with housing 9, such that motion of housing 9 is transferred and/or converted to an adjustment of a position, e.g. the longitudinal position, of support member 4 by virtue of matching threading between nut 11 and support member 4. In some embodiments, not depicted in FIG. 1, the motion of mounting plate 8 may be transferred and/or converted to rotational motion of support member 4 rather than a non-rotating motion. Nut 11 may not be readily visible in a non-exploded view of tilt system 10. Support member 4 may be translating, e.g. moving without angular displacement, such as a translating screw. Alternatively and/or simultaneously, support member 4 may be non-rotating. Support member 4 may be a trapezoidal screw. The various embodiments of support member 4 may be combined, for example support member 4 may be a non-rotating translating trapezoidal lead screw.

Figure 2:
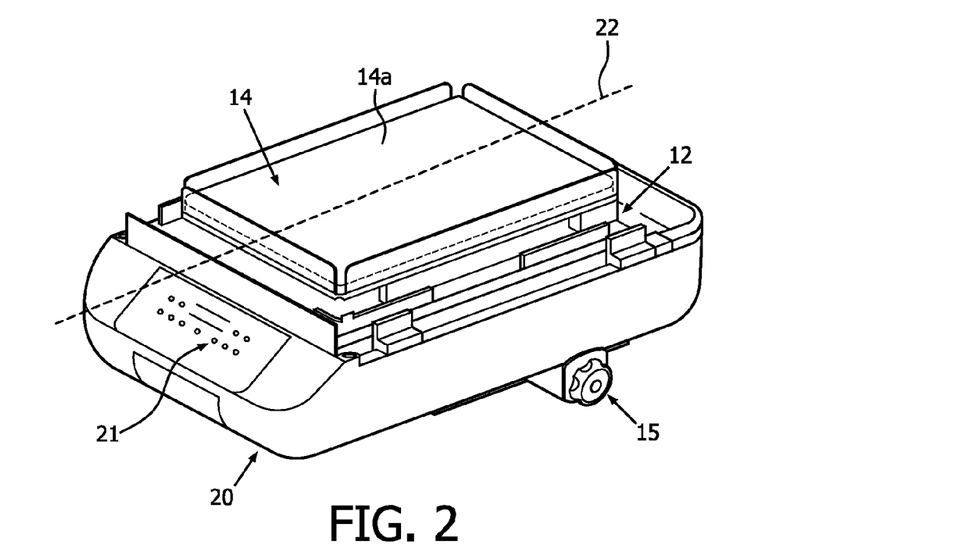
FIG. 2 illustrates an isometric view of an infant-supporting device in accordance with one or more embodiments.

FIG. 2 illustrates an isometric view of infant-care medical device 20 and infant-supporting device 14 in accordance with one or more embodiments. An infant may be placed on and/or supported by infant-supporting device 14 such that an area 14a may be a thermo-regulated area, sterile area, and/or an area within which a suitable environment is intended to be maintained for the benefit of the infant. Tilt platform 12 may have a center axis 22 that divides tilt platform 12 in a left half and a right half. Center axis 22 may be part of a center plane that divides infant-care medical device 20 and infant-supporting device 14 in a left half and a right half. Infant-care medical device 20 may include a control panel 21, which may for example be configured to control the temperature and/or other factors of the suitable environment of area 14a. First actuator 15 is disposed outside of area 14a and receives actuation outside of area 14a, as does a second actuator similar to second actuator 17 of FIG. 1, the second actuator being obscured from view in FIG. 2.

Combining FIG. 1 and FIG. 2, first actuator 15 and second actuator 17 are disposed on opposite sides relative to infant-supporting device 14 such that, e.g., a caregiver may conveniently tilt tilting platform 12 from either side of infant-supporting device 14 while maintaining the integrity of the environment of area 14a. Conveniently, tilt system 10 allows single-handed adjustments to the tilt angle of tilt platform 12.

Combining FIG. 1, FIG. 2, and FIG. 3, support member 4 may be disposed a predetermined center-offset from center axis 22. The predetermined center-offset may be about 50 mm, about 60 mm, about 70 mm, about 80 mm, about 90 mm, about 100 mm, about 110 mm, about 120 mm, at least 80 mm, at least 100 mm, at least 120 mm, and/or another suitable distance such that under-surface phototherapy for subject 106 and/or (x-ray) photography of an area at or near center axis 22 is allowed and/or undisrupted by support member 4. Alternatively, and/or simultaneously, support member 4 may be disposed a predetermined axial offset from tilt axis 16. The predetermined axial offset may be about 150 mm, about 160 mm, about 170 mm, about 180 mm, about 190 mm, about 200 mm, about 210 mm, about 220 mm, at least 180 mm, at least 190 mm, at least 200 mm, at least 220 mm, and/or another suitable distance such that under-surface phototherapy for subject 106 and/or (x-ray) photography of an area at or near center axis 22 is allowed and/or undisrupted by support member 4. For example, known devices that provide under-surface phototherapy may range in length from about 50 cm to about 75 cm, in width from about 28 cm to about 44 cm, and in height from about 11 cm to about 16 cm. While future devices that provide under-surface phototherapy may be more compact than the known devices, using, for support member 4, an axial offset from tilt axis 16 and/or a center-offset from center axis 22 will allow (better) under-surface phototherapy compared to using a tilt mechanism that is located centrally under a tilt platform, infant-supporting device, and/or infant-care medical device. In some embodiments of tilt system 10, such as may be used with certain common types of baby warmers, a centrally-located support member 4, e.g. at or near center axis 22 and/or at or near centrally located tilt axis 16, would not leave enough space to allow under-surface phototherapy for at least some of the described known devices.

In some embodiments, tilt axis 6 may be located at or near one end of tilt platform 12. In such cases, support member 4 may be disposed at or near the opposite end of tilt platform 12, at a predetermined axial offset of about 300 mm, about 325 mm, about 350 mm, about 375 mm, about 400 mm, about 450 mm, and/or another suitable distance such that use of under-surface phototherapy is allowed, for example for a baby warmer.

Referring to FIG. 3, support member 4, as depicted, is fully extended upward and outward of housing 9 such that tilt angle $\alpha$ of tilt platform 12 is currently at its positive maximum within the range of angles defined for operation of tilt system 10. In various embodiments, the range of angles may be from about −30 degrees to about +30 degrees, from about −20 degrees to about +20 degrees, from about −15 degrees to about +15 degrees, from about −12 degrees to about +12 degrees, from about −10 degrees to about +10 degrees, and/or another range of degrees suitable to accomplish one or more particular benefits for infants during use. The range of angles may be asymmetrical around zero degrees. The range of angles, together with the distance between support member 4 and tilt axis 16 are factors in the required length of support member 4.

Figure 4:
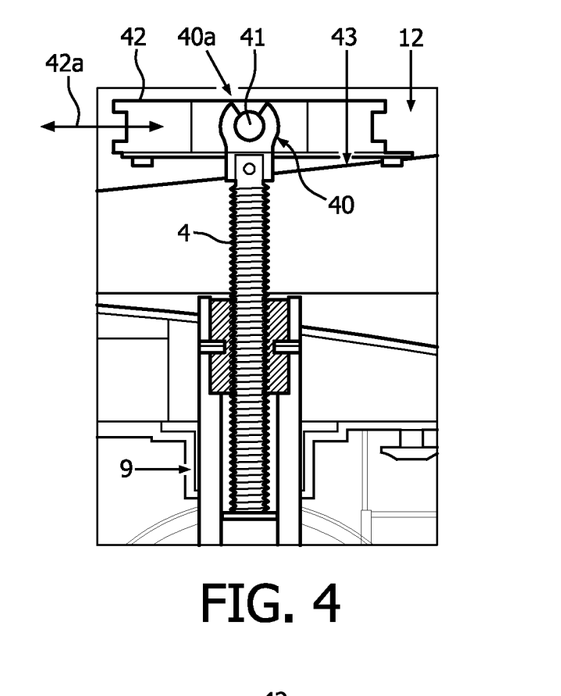
FIG. 4 illustrates various components of a system for tilting in accordance with one or more embodiments.

Referring to FIG. 1, tilt system 10 may include clevis 40, mechanically coupled to distal end 4a of support member 4, e.g. through dowel pin 19. Support member 4 may be mechanically coupled to the tilt platform and/or a component thereof through a pivot pin that matches clevis 40. As the position of support member 4 with respect to housing 9 is adjusted, e.g. longitudinally without angular displacement, the point of engagement with the tilt platform moves horizontally and/or laterally relative to the tilt platform. By way of illustration, FIG. 4 illustrates various components that may be used to couple, e.g. mechanically, support member 4 to tilt platform 12 and accommodate the movement of the point of engagement with tilt platform 12. In particular, clevis 40 mechanically engages a pivot pin 41. Clevis 40 and pivot pin 41 form one contemplated version of a manual coupler or decoupler, since the pin 41 can be disengaged from the clevis 40 without use of a tool or instrument. Pivot pin 41 is held within, or otherwise coupled to horizontally movable guide block 42, which can move in a direction 42a relative to the position within tilt platform 12. In some embodiments, horizontally movable guide block 42 is held within a cavity, chamber, and/or other suitable enclosure of tilt platform 12 by a fixed retainer plate 43. As support member 4 moves, e.g. upward and outward of housing 9, the adjustment of the rotational orientation of tilt platform 12 forces movement along direction 42a of horizontally movable guide block 42. In some embodiments, a pivot pin may be coupled with the distal end of support member 4, and a matching clevis may be held within a guide block coupled to and/or held within a tilt platform similar to tilt platform 12.

Referring to FIG. 1, in some embodiments, support member 4 is configured such that tilt system 10 rigidly locks at some, most, or all tilt angles within the range of tilt angles defined for operation of tilt system 10, in light of one or more of a particular coefficient of friction of support member 4 with nut 11 and/or housing 9, a maximum length of travel of support member 4 during use, a mean diameter of support member 4, a predetermined number of rotations of support member 4 to fully adjust the tilt of tilt platform 12, a maximum weight forcing down on support member 4, and/or other considerations that could be a factor in rigidly locking support member 4 such that support member 4 does not back drive. Locking in this fashion may be referred to as self-locking. In some embodiments, a self-locking tilt system may not require an external and/or additional brake mechanism during operation. Examples of external and/or additional brake mechanisms include brake pads, spring-loaded brakes, lockable gas springs, index locking, and/or other brake mechanisms. In a preferred embodiment, a helix angle of support member 4 ranges between about 6 and about 9 degrees, between about 7 and about 8 degrees, and/or within another range suitable to rigidly lock as described herein. The predetermined number of rotations required to accomplish a full tilt of +12 degrees may range between about 6 and about 9 rotations, between about 8 and about 10 rotations, between about 9 and about 11 rotations, and/or within another suitable range of rotations. In some embodiments, fewer rotations may be required by adjusting the gear ratio of gearbox 6, for example to a 1:2 ratio.

The maximum length of travel of support member 4 depends on the predetermined distance between the point of engagement of support member 4 with tilt platform 12 and tilt axis 16, as well as the desired range of tilt angles, and/or other considerations. The distance between the point of engagement of support member 4 with tilt platform 12 and tilt axis 16 may be about 160 mm, about 180 mm, about 190 mm, about 200 mm, about 220 mm, between about 170 mm and about 200 mm, between about 190 mm and about 210 mm, and/or other suitable distances for a centrally located tilt axis 16, or twice such a distance for embodiments in which tilt axis 16 is disposed on the opposite end of tilt platform 12 from support member 4. The maximum length of travel of support member 4 during use over the defined range of angles may be about 80 mm, about 90 mm, about 100 mm, about 120 mm, between about 80 mm and about 110 mm, between about 90 mm and about 130 mm, and/or another suitable range for the maximum length of travel of support member 4 for a centrally located tilt axis 16, or twice such a length for embodiments in which tilt axis 16 is disposed on the opposite end of tilt platform 12 from support member 4. The pitch of support member 4 may be about 5 mm, about 6 mm, about 7 mm, about 8 mm, and/or another suitable pitch for self-locking. The mean diameter of support member 4 may be about 12 mm, about 14 mm, about 15 mm, about 16 mm, about 18 mm, between about 12 mm and about 14 mm, and/or another suitable diameter. The coefficient of friction, which may also be referred to as p, of support member 4 may be about 0.08, about 0.1, about 0.12, about 0.14, and/or another suitable coefficient of friction. In a preferred embodiment, support member 4 may have a diameter of about 13 mm, a pitch of about 5 mm, a coefficient of friction of about 0.13, a maximum tilt of 12 degrees, and a length of travel of about 90 mm. A lower coefficient of friction, e.g. about 0.1, may be compensated for in various ways, including using a support member 4 having a pitch of about 4 mm to maintain self-locking. The maximum weight forcing down on support member 4 during normal operation of tilt system 10 may be about 10 lbs, about 15 lbs, about 20 lbs, about 25 lbs, about 30 lbs, between about 15 lbs and 25 lbs, and/or another suitable weight limit that includes the tilt platform, all or some of the infant-supporting device, one or more infants, and/or other objects/components. For ease of use, the maximum torque required for operating tilt system 10 through first actuator 15 or second actuator 17 may be about 0.1 Nm, about 0.2 Nm, about 0.3 Nm, about 0.4 Nm, about 0.5 Nm, and/or another suitable amount of torque for (manual) operation.

In some embodiments, tilt system may be driven by a motor, for example controlled through control panel 21. In such cases, the maximum torque required for manual operation may not be a consideration in ease-of-use.

Figure 5:
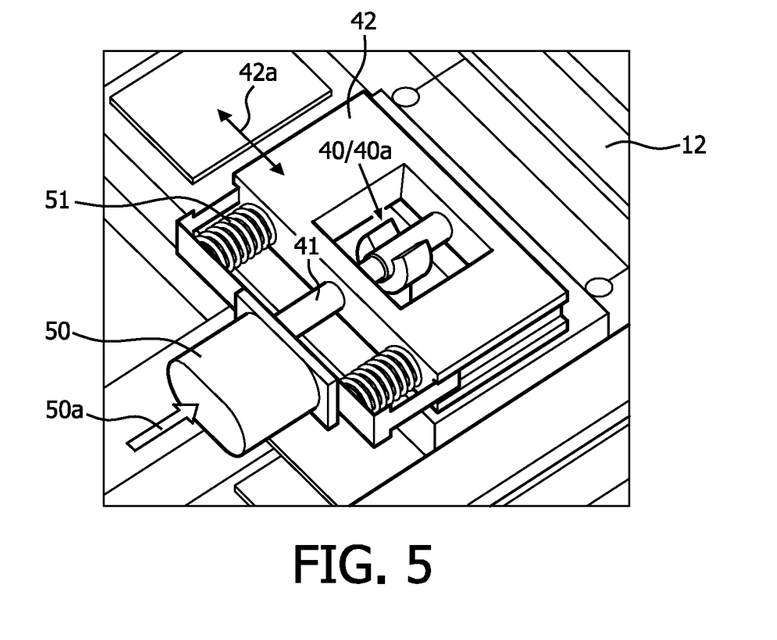
FIGS. 5-7 illustrate various components related to a release mechanism to decouple a tilt platform from a support member in accordance with one or more embodiments.
Figure 6:
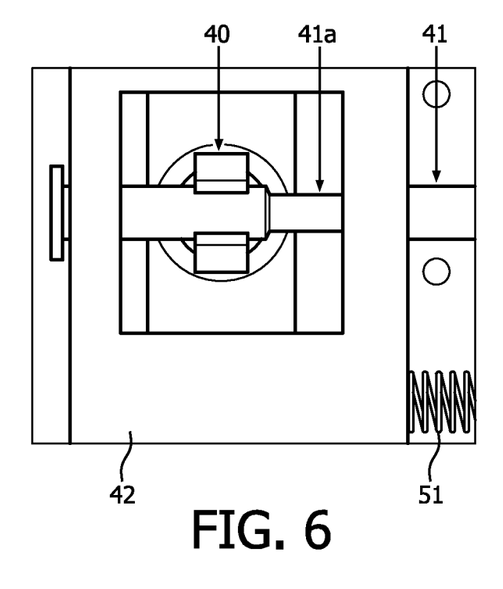
Figure 7:
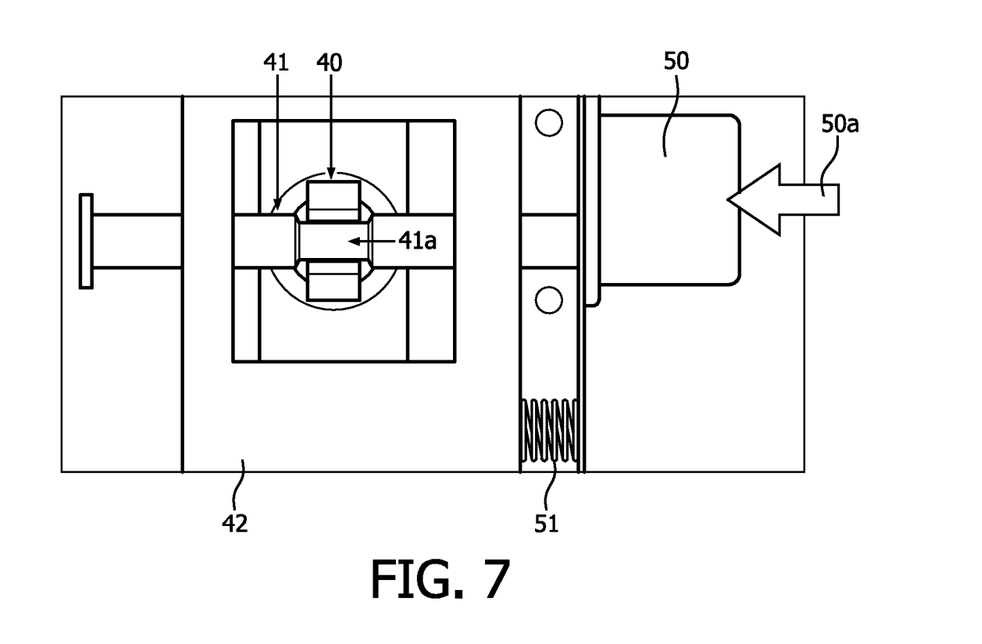

FIGS. 5-7 illustrate various components related to a release mechanism to decouple tilt platform 12 from support member 4. Referring to FIG. 5, clevis 40 may include an open end 40a. Referring to FIG. 6, pivot pin 41 may include a segment 41a having a reduced diameter. Referring to FIG. 7, pivot pin 41 may be mechanically coupled, for example through one or more springs 51, to release actuator 50 such that release actuator 50 is movable in a direction 50a. Movement of release actuator 50 moves pivot pin 41 correspondingly such that segment 41a of pivot pin 41 may be aligned with open end 40a of clevis 40. Responsive to such an alignment, clevis 40 may be mechanically decoupled from tilt platform 12, for example by lifting tilt platform 12 manually. As depicted in FIG. 6, during normal tilting operation segment 41a and open end 40a may not be aligned. As depicted in FIG. 7, upon receiving actuation by release actuator 50, segment 41a and open end 40a may be aligned to allow decoupling as described above. Easy access to tilt system 10 and/or any of its constituent components may be needed to sanitize, clean, and/or service to ensure proper operation.

Figure 8:
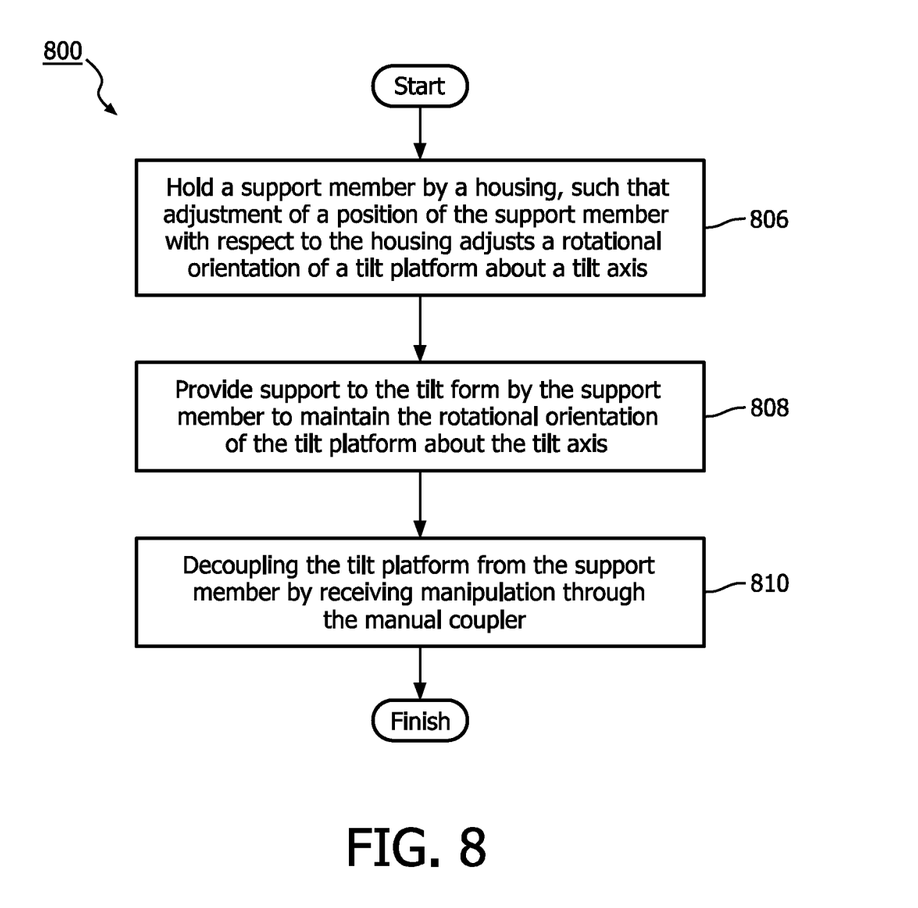
FIG. 8 illustrates a method for tilting an infant-supporting device in accordance with one or more embodiments.

FIG. 8 illustrates method 800 for supporting an infant within a thermo-regulated area of an infant-supporting device using a tilt system having a tilt platform disposed below the infant-supporting device that tilts about a tilt axis, a first actuator, a second actuator, a housing disposed below the tilt platform, and a support member. The operation of method 800 presented below is intended to be illustrative. In certain embodiments, method 800 may be accomplished with one or more additional operations not described, and/or without one or more of the operations discussed. Additionally, the order in which the operations of method 800 are illustrated in FIG. 8 and described below is not intended to be limiting.

In certain embodiments, method 800 may be implemented using one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 800 in response to instructions stored electronically on an electronic storage medium. The one or more processing devices may include one or more devices configured through hardware, firmware, and/or software to be specifically designed for execution of one or more of the operations of method 800.

At an operation 806, a support member is held by a housing such that a position of the support member with respect to the housing is adjustable, wherein adjustment of the position of the support member with respect to the housing adjusts a rotational orientation of the tilt platform about the tilt axis. The adjustment of the position of the support member is accomplished through a manual coupler that couples the tilt platform to the support member. In some embodiments, operation 806 is performed by a housing and nut the same as or similar to housing 9 and nut 11 (shown in FIG. 1 and described herein). Alternatively, and/or simultaneously, in some embodiments, operation 806 is performed by a manual coupler the same as or similar to the combination of clevis 40 and pivot pin 41 (shown in FIG. 4 and described herein).

At an operation 808, support to the tilt platform is providing by a support member to maintain the rotational orientation of the tilt platform about the tilt axis. In some embodiments, operation 808 is performed by a support member the same as or similar to support member 4 (shown in FIG. 1 and described herein).

At an operation 810, the tilt platform is decoupled from the support member by receiving manipulation through the manual coupler. In some embodiments, operation 810 is performed by a manual coupler the same as or similar to the combination of clevis 40, pivot pin 41, and release actuator 50 (shown in FIG. 5 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system for tilting an infant-supporting device having a thermo-regulated area, the system comprising:
    a tilt platform configured to be disposed below the infant-supporting device, wherein the tilt platform is configured to tilt about a tilt axis;
    a housing disposed below the tilt platform;
    a support member, the support member providing support to the tilt platform to maintain a rotational orientation of the tilt platform about the tilt axis, wherein the support member is held by the housing such that a position of the support member with respect to the housing is adjustable, and wherein adjustment of the position of the support member with respect to the housing adjusts the rotational orientation of the tilt platform about the tilt axis;
    an actuator operable to adjust the position of the support member with respect to the housing, thereby adjusting the rotational orientation of the tilt platform, and wherein the actuator is disposed and actuated outside of the thermo-regulated area of the infant-supporting device; and
    a manual coupler that couples the tilt platform to the support member, wherein the manual coupler is pivotally coupled to the tilt platform through a pivot structure,
    wherein the adjustment of the position of the support member is actuated through the manual coupler, and wherein the manual coupler is configured to decouple the tilt platform from the support member by receiving manipulation.

2. The system of claim 1, wherein the manual coupler comprises:
    a clevis coupled to the support member;
    the pivot structure configured to fit through the clevis, wherein the adjustment of the position of the support member is actuated through a mechanical engagement between the pivot structure and the clevis.

3. The system of claim 2, further comprising:
    a horizontally movable guide block coupled to the tilt platform, wherein the horizontally movable guide block is configured for horizontal movement relative to the tilt platform, wherein the pivot structure is coupled to the tilt platform through a coupling with the horizontally moveable guide block, and wherein the horizontal movement is based on the tilt of the tilt platform.

4. The system of claim 3, wherein the clevis includes an open end, wherein the pivot structure includes a segment having a reduced diameter, wherein the reduced diameter is arranged to fit through the open end of the clevis, and wherein decoupling the tilt platform from the support member is accomplished manually after aligning the segment of the pivot structure having the reduced diameter with the clevis.

5. The system of claim 4, further comprising a release actuator coupled to the pivot structure, wherein the release actuator is operable to align the segment of the pivot structure having the reduced diameter with the clevis by receiving actuation.

6. A method for supporting an infant with an infant-supporting device using a tilt system having a tilt platform disposed below the infant-supporting device that tilts about a tilt axis, an actuator, a support member, a manual coupler that couples the tilt platform to the support member, and a housing disposed below the tilt platform, the method comprising:
    holding the support member by the housing such that a position of the support member with respect to the housing is adjustable through actuation received by the actuator, wherein adjustment of the position of the support member with respect to the housing adjusts a rotational orientation of the tilt platform about the tilt axis, wherein the adjustment of the position of the support member is actuated through the manual coupler, wherein the manual coupler is pivotally coupled to the tilt platform through a pivot structure;
    providing support to the tilt platform by the support member to maintain the rotational orientation of the tilt platform about the tilt axis; and
    decoupling the tilt platform from the support member by receiving manipulation through the manual coupler.

7. The method of claim 6, the manual coupler comprising a clevis and the pivot structure configured to fit through the clevis, wherein the clevis is coupled to the support member, and wherein the adjustment of the position of the support member is actuated through a mechanical engagement between the pivot structure and the clevis.

8. The method of claim 7, the tilt system further having a horizontally movable guide block coupled to the tilt platform, the horizontally moveable guide block being configured for horizontal movement relative to the tilt platform, wherein the pivot structure is coupled to the tilt platform through a coupling with the horizontally moveable guide block, and wherein the horizontal movement of the horizontally moveable guide block is based on the tilt of the tilt platform.

9. The method of claim 8, wherein the clevis includes an open end, wherein the pivot structure includes a segment having a reduced diameter, wherein the reduced diameter is arranged to fit through the open end of the clevis, and wherein decoupling the tilt platform from the support member is accomplished by aligning the segment of the pivot structure having the reduced diameter with the clevis.

10. The method of claim 9, the tilt system further having a release actuator coupled to the pivot structure, wherein aligning the segment of the pivot structure having a reduced diameter with the clevis is accomplished by receiving actuation through the release actuator.

11. A system configured for supporting an infant with an infant-supporting device, the system comprising:
   tilt means disposed below the infant-supporting device for tilting the infant-supporting device about a tilt axis;
   lifting means having a position with respect to a housing means that is disposed below the tilt means, wherein the position of the lifting means is adjustable, wherein adjustment of the position with respect to the housing means adjusts a rotational orientation of the tilt means about the tilt axis;
   support means for providing support to the tilt means to maintain the rotational orientation of the tilt means about the tilt axis;
   actuator means for receiving actuation, wherein actuation of the actuator means actuates an adjustment of the position of the lifting means with respect to the housing means, thereby adjusting the rotational orientation of the tilt means; and
   coupling means for coupling the tilt means to the support means, wherein the coupling means is pivotally coupled to the tilt means through a pivot structure, wherein the adjustment of the position of the lifting means with respect to the housing means is actuated through the coupling means, and wherein the coupling means is configured to decouple the tilt means from the support means by receiving manipulation.

12. The system of claim 11, wherein the coupling means includes a clevis coupled to the lifting means and the pivot structure configured to fit through the clevis, wherein the adjustment of the position of the lifting means with respect to the housing means is actuated through a mechanical engagement between the pivot structure and the clevis.

13. The system of claim 12, further comprising:
   movable means coupled to the tilt means, the moveable means configured for horizontal movement relative to the tilt means, wherein the pivot structure is coupled to the tilt means through a coupling with the moveable means, and wherein horizontal movement of the movable means is based on the tilt of the tilt means.

14. The system of claim 13, wherein the clevis includes an open end wherein the pivot structure includes a segment having a reduced diameter, wherein the reduced diameter is arranged to fit through the open end of the clevis, and wherein decoupling the tilt means from the support means is accomplished manually by aligning the segment of the pivot structure having the reduced diameter with the clevis.

15. The system of claim 14, further comprising release means coupled to the pivot structure, wherein the release means is operable to align the segment of the pivot structure having the reduced diameter with the clevis.

* * * * *